United States Patent [19]

Christensen et al.

[11] 4,079,179

[45] Mar. 14, 1978

[54] 6-LOWERALKOXY OR LOWERALKYLTHIO-3-CEPHEM-4-CARBOXYLIC ACIDS

[75] Inventors: Burton G. Christensen, Metuchen; Ronald W. Ratcliffe, Matawan, both of N.J.

[73] Assignee: Merck & Co., Inc., Rahway, N.J.

[21] Appl. No.: 671,785

[22] Filed: Mar. 30, 1976

[51] Int. Cl.$^2$ .................. C07D 501/34; C07D 501/30; C07D 501/18; C07D 501/08

[52] U.S. Cl. ........................................ 544/28; 544/29; 544/30; 544/53; 260/455 A; 424/246

[58] Field of Search ............... 260/243 C; 544/28, 29, 544/30

[56] References Cited

U.S. PATENT DOCUMENTS

| 3,900,487 | 8/1975 | Elphinstone et al. | 260/243 C |
| 3,954,731 | 5/1976 | Spitzer | 260/243 C |
| 3,962,224 | 6/1976 | Christensen et al. | 260/243 C |
| 3,975,383 | 8/1976 | Mayler et al. | 260/243 C |

OTHER PUBLICATIONS

Guthikonda et al., JACS 96 7584 (1974).
Vanderhaeghe et al., J. Med. Chem. 18 486 (1975).
Ratcliffe et al., Tetrahedron Letters 4645 (1973).
Ratcliffe et al., Tetrahedron Letters 4649 (1973).
Ratcliffe et al., Tetrahedron Letters 4653 (1973).
Steinberg et al., Tetrahedron Letters 3567 (1974).
Firestone et al., J. Org. Chem. 3384 (1974).
Firestone et al., J. Org. Chem. 437 (1974).
Cama et al., JACS 96 7582 (1974).

*Primary Examiner*—Donald G. Daus
*Assistant Examiner*—Diana G. Rivers
*Attorney, Agent, or Firm*—Hesna J. Pfeiffer; Julian S. Levitt

[57] ABSTRACT

Cephalosporin compounds having a loweralkoxy or loweralkylthio substituent in the 6-position are prepared by a multi-step total synthesis route using as starting material a glycine ester, which first is reacted to yield a dihydrothiazine, and subsequently condensed with azidoacetyl chloride to form the cepham nucleus, then dehydrated to yield the desired 3-unsaturation. Subsequent reduction and acylation steps are analogous to known chemistry, and yield the novel 6-loweralkoxy- or loweralkylthio-7-amino intermediates and the antibacterially active 6-loweralkoxy or loweralkylthio-7-acylamido end products.

10 Claims, No Drawings

6-LOWERALKOXY OR LOWERALKYLTHIO-3-CEPHEM-4-CARBOXYLIC ACIDS

This application relates to novel antibiotic compounds and intermediate products used to prepare them. A novel synthetic route is provided for this total synthesis.

The compounds of this invention can be represented by the following formula:

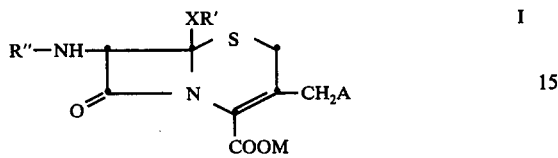

wherein X is oxygen or sulfur and R' is loweralkyl, wherein R" is hydrogen, or

wherein $R_{10}$ is hydrogen, amino, hydroxy, or carboxyl, and $R_{11}$ is phenyl, thienyl, furyl, or tetrazolyl; and A is loweralkanoyloxy, hydrogen, carbamoyloxy, N-methyltrizinylthio, N-methyl-1,2,3,4-tetrazolylthio, or 5-methyl-1,3,4-thiadiazo-2-yl-thio.

The terms "loweralkyl", and "loweralkanoyloxy" represent straight or branched carbon chains having 1-5 carbon atoms.

In addition to the free carboxylic acids described above, this invention also includes commonly employed salts and esters, such as pharmaceutically acceptable non-toxic salts, including sodium, potassium, calcium, etc., and easily removable or labile esters, such as benzyl, methoxymethyl, benzhydryl, benzyloxymethyl, phenoxymethyl, m-phenoxybenzyl, or 3-methyl-3-butenyl, pivaloyloxymethyl, p-tert-butylbenzyl, etc.

Also, this invention contemplates other compounds in which A can be any of a number of other substituents well known in the art. These are formed from the 3-acetoxymethyl side chain, which can be condensed with the appropriate thiol to yield the pyridinium or thioheterocyclic group, or which can be transformed into the 3-hydroxymethyl derivative which can be further substituted to yield the carbamoyloxy, substituted carbamoyloxy, thiocarbamoyloxy, or substituted thiocarbamoyloxy. The reactions involved in these transformations can be carried out when R" is as defined above, i.e., either on the 7-amino intermediate or 7-acylamino end product.

In accordance with this invention, the compounds above can be prepared using the following processes represented schematically.

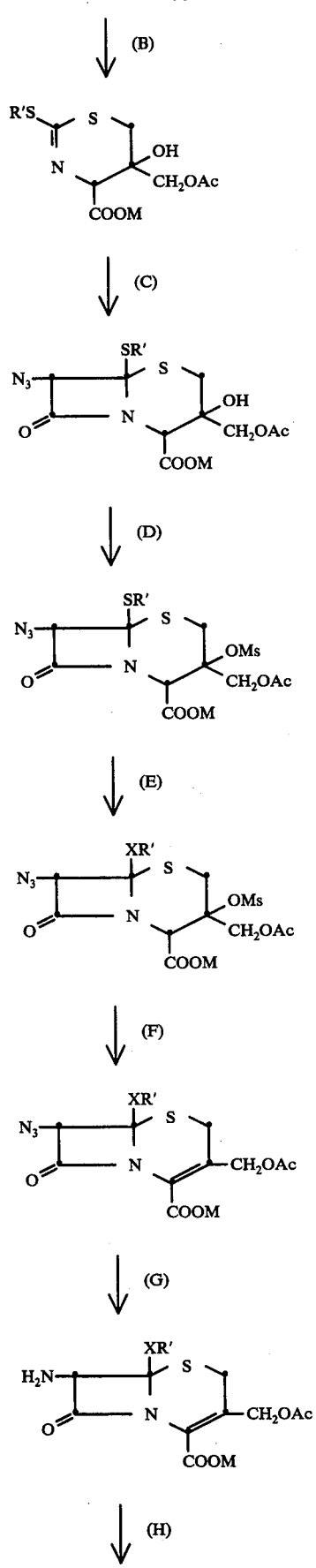

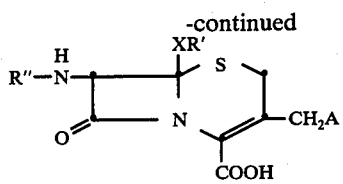

In the flow sheet above, the symbols X, R', A and R" are the same as defined in Formula I.

M is used to indicate a carboxy protecting group preferably one which can later be easily removed to obtain the free acid form of the cephalosporin without description of the β-lactam moiety. Protecting groups suitable for this purpose are indeed well known in this art. Examples of suitable protecting ester groups that might be mentioned are those of alcohols, phenols, and the like, wherein M can be an alkyl, or aralkyl group containing from 1 to about 20 carbon atoms. Thus, M can be a lower alkyl group such as methyl, ethyl or tertiary butyl, a substituted alkyl such as phthalimidomethyl, pivaloyloxymethyl, phenoxymethyl, succinimidomethyl, phenacyl, substituted phenacyl such as p-bromophenacyl, a β-substituted ethyl group such as 2,2,2-trichloroethyl, 2-methylthioethyl or 2-(p-methylphenyl)ethyl, an alkenyl group such as 3-butenyl, propenyl, allyl, 3-methyl-3-butenyl, etc., an alkoxyalkyl group such as methoxymethyl, an aryloxyalkyl such as p-methoxyphenoxymethyl, an aralkyloxyalkyl group such as benzyloxymethyl, benzyl, or a substituted benzyl group such as p-nitrobenzyl, p-methoxybenzyl, 3,5-dinitrobenzyl, 2,4,6-trimethylbenzyl, p-t-butylbenzyl, or 3,5-dichloro-4-hydroxybenzyl, benzhydryl or a substituted benzhydryl group such as p-methoxybenzhydryl, and the like. Preferred blocking groups are methyl, tertiary butyl, phenacyl, p-bromophenacyl, p-nitrobenzyl, 2,2,2-trichloroethyl, p-methoxybenzyl, benzhydryl, m-methoxybenzyl and p-methoxyphenoxymethyl.

Ac indicates the acetyl group,

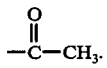

The processes outlined in this flow sheet are described in more detail below.

Process (A) uses a glycine ester in reaction with carbon disulfide in an inert solvent media made basic by addition of a tertiary amine, followed by reaction with an alkylating agent such as loweralkyl iodide, e.g., methyl iodide, ethyl iodide, propyl iodide, or isopropyl iodide. The solvent can be dioxane, tetrahydrofuran, dimethoxyethane, or ethanol. The temperature range of this step can be between 0°–100° C., although temperature is not normally a critical parameter, and an ambient temperature is generally convenient.

Step (B) of the process comprises reacting the previously prepared dithiocarbamoyl intermediate with a substituted acetoxy acetone of the general formula

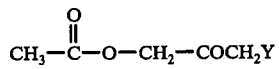

or

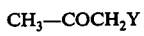

wherein Y is bromo, iodo, chloro, mesyloxy, tosyloxy, or trifluoromethyl sulfonyloxy, preferably chloro or iodo. The acetoxy acetone is used to prepare compounds having the 3-acetoxymethyl side chain (—CH$_2$A wherein A is acetoxy). The halo acetone, Ch$_3$COCH$_2$Y can be conveniently used to prepare the corresponding 3-methyl side chain (—CH$_2$A wherein A is hydrogen). Also when other loweralkanoyloxy substituents are desired (A = lower alkanoyloxy), then the appropriate lower alkanoyloxy acetone is used, e.g.,

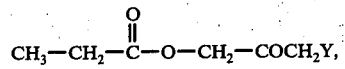

when A is propionyloxy. (It is most convenient to prepare the iodo form in situ by first using the chloro form, then adding sodium iodide or the like to the reaction mixture.) The reaction may be carried out at temperatures varying from 0°–50° C. in the presence of 1–5 equivalents of one or more bases such as triethylamine, an alkali metal carbonate such as potassium carbonate, phenyl lithium, an alkali metal hydryde such as sodium hydride, diazobicyclononene, bis-1,8-(dimethylamino) napthalene and the like. Following this reaction, which is more properly characterized as a series of reactions, as each reagent can be sequentially added, the corresponding dihydrothiazine is prepared.

Step (C) involves the reaction of the dihy0rothiazine compound with an azidoacetyl reagent in the presence of an acid scavenger and preferably in a solvent medium at temperatures varying from −78° to 30° C. to afford the corresponding 7-azido beta-lactam compound.

The azidoacetyl reactants of particular interest have the following formula:

wherein and Z is halogen, OSO$_2$CF$_3$ or OSO$_2$CH$_3$. The reaction is preferably carried out at low temperatures, for example at about 8° C., and in the presence of a sufficient amount of base such as a tertiary amine which serves as an acid scavenger and, in addition, catalyzes the cyclization of the intermediate dihydrothiazine compound. Thus, the reaction is conveniently carried out adding a solution of the azide in methylene chloride to a cool solution of the dihydrothiazine and a tertiary amine such as triethylamine in the same solvent; the amine being present in slight excess of the molar equivalent amount. The reaction mixture is stirred in the cold until the formation of the desired 7-azido cepham compound is complete.

Step (D) prepares the 3-blocked hydroxy compound, wherein Ms is methyl sulfonyl, by reaction with methyl sulfonyl chloride. This latter intermediate can then, if desired, (Step E) be transformed into the corresponding 6-loweralkoxy compound by reaction with thallium salts, such as thallium trinitrate in the presence of lower alkanol in an inert solvent.

The 7-axido-6-XR' intermediate is then dehydrated to yield the desired 3-unsaturated compound, Step F. This dehydration can be accomplished by reaction with a base as triethylamine in an anhydrous inert solvent, e.g., methylene chloride, or by treatment with silica gel in an inert solvent, e.g., benzeneethylacetate.

The reduction to the amine, Step G, is conveniently effected with hydrogen in the presence of a noble metal catalyst such as platinum oxide, aluminum amalgam, zinc and acetic acid or copper and thiophenol in accordance with methods known in this art.

Step H represents a number of steps, all of which are processes well known in the art. The acylation of amino groups is accomplished using the appropriate acylating agent. The cleavage of ester groups M can be readily removed in accordance with processes known in this art. For example, benzyl, or p-nitrobenzyl is removed by catalytic hydrogenation and is accomplished in Step G. Other common ester groups such as benzhydryl, tertiary butyl, p-methoxybenzyl and p-methoxyphenoxymethyl groups are cleaved with an acid such as trifluoroacetic acid and the 2,2,2-trichloroethyl and phenacyl groups are cleaved by reaction with zinc and acetic acid. The term "blocking group" as utilized herein is employed in the same manner and in accordance with the teaching of U.S. Pat. No. 3,697,515; the contents therein with respect to said blocking group being incorporated herein by reference.

In addition, the 3-acetoxymethyl can be converted to or readily replaced by other A substituents pursuant to methods well known in this art. For example, upon treating the 3-acetoxymethyl substituted cephalosporanates of this invention with a suitable reagent or combination of reagents, it is possible to substitute various substituents for acetoxy at the 3-position of the cephalosporin nucleus, or after cleavage to the 3-hydroxymethyl compound.

Thus, by reaction with a quaternary ammonium compound, for example pyridine, the 3-acetoxy cephalosporin, is converted to the corresponding 3-pyridinomethyl compound. Alternatively, the 3-acetoxy cephalosporins upon treatment with citrus acetylesterase are converted to the corresponding 3-hydroxymethyl compounds which can be acylated to produce other 3-acyloxymethyl including carbamoyloxymethyl. The 3-heteroarylthio substituents are prepared by displacing the 3-acetoxymethyl cephalosporin with the analogous mercaptan under basic conditions. Similarly, other 3-substituted cephalosporin compounds are prepared following procedures well known in this art.

The compounds obtained by the processes of this invention, that is of Formula I, except where R" is amino, are active against some pathogenic gram-negative and gram-positive bacteria, for example, *Corynebacterium diptheriae*. They can be used to treat antibacterial infections in humans and animals and are employed for this use analogously to other commercially available cephalosporins. As such, most commonly used are sterile solutions for injection purposes, using the water soluble salts, such as sodium or potassium salts. Dosage levels are comparable to other known cephalosporins. In addition, they can be used for industrial antiseptic solutions in concentrations of 1–100 parts per 1–6 parts solution. The compounds of Formula I when R" is amino do not possess significant antibacterial activity, but are useful primarily as intermediate compounds to prepare the antibacterially active end products.

This invention is further illustrated by the following examples. The compounds containing one or more asymmetric carbon atoms exist as racemic compounds. These compounds can be resolved if desired by procedures known in the art.

EXAMPLE 1

Sodium 7-(2-Thienylacetamido)-6-Methylthio-3-Acetoxymethyl-3-Cephem-4-Carboxylate Step A: p-Nitrobenzyl-N-Methylthiothiono-Glycinate p-Nitrobenzyl glycinate hydrobromide (7.15 g., 24.6 mMol) is suspended in $H_2O$ (15 ml.) and the mixture is layered with EtOAc (40 ml.). The mixture is cooled in ice and stirred while cold, saturated aqueous $K_2CO_3$ (6 ml.) is added. The layers are separated and the aqueous portion is extracted with more EtOAc (3 × 15 ml.). The combined EtOAc solution is dried over $Na_2SO_4$, filtered and evaporated in vacuo to provide p-nitrobenzyl glycinate (5.05 g., 24.0 mMol, 98% yield) as an off-white solid.

The above amino ester is dissolved in anhydrous dioxane (45 ml.) and the solution is cooled in an ice-bath. $Et_3N$ (3.35 ml., 24 mMol) and $CS_2$ (1.52 ml., 25 mMol) are added. The flask is stoppered and the solution is stirred at room temperature for 1 hr. The solution is again cooled in ice and MeI (1.56 ml., 25 mMol) is added. The cooling bath is removed and the mixture is stirred at room temperature for 1 hr. The mixture is filtered and the filtrate is evaporated in vacuo. The residue is taken up in EtOAc (100 ml.) and the solution is washed with $H_2O$ (3 × 50 ml.) and brine, dried with $MgSO_4$, filtered, and evaporated in vacuo to an off-white solid. Recrystallization of the crude product from $CH_2Cl_2$-petroleum ether provides p-nitrobenzyl N-methylthiothiono-glycinate (6.65 g.) as a cream colored solid. The mother liquors yield more product (0.36 g.), raising the total yield to 97%. The product has mp 105° C.; ir (Nujol) 3.00 (NH), 5.80 (C=O), 6.63, and 7.41μ; nmr $(CDCl_3)\delta$ 2.65 (s, 3, S$CH_3$), 4.57 (d,2, J=5 Hz, HN$CH_2$), 5.33 (s,2, $CH_2$Ar), 7.53 (d,2, J=9Hz, ArH) and 8.23 (d,2, J=9Hz, ArH); mass spectrum m/e 300 (M+), 252, 164, 136, and 106.

Anal. Calculated for $C_{11}H_{12}N_2O_4S_2$: C, 43.99; H, 4.03; N, 9.33; S, 21.35. Found: C, 44.13; H, 4.08; N, 9.47; S, 21.22.

Step B: p-Nitrobenzyl 2-Methylthio-5-hydroxy-5-acetoxymethyl-5,6-dihydro-4H-1,3-thiazine-4-carboxylate 1-Acetoxy-3-chloro-2-propanone (2.55 g., 16.95 mMol) is dissolved in acetone (30 ml.) and the solution is treated with NaI (2.54 g., 16.95 mMol). The resulting mixture is stirred at room temperature for 5 mins. p-Nitrobenzyl N-methylthiothiono-glycinate (5.09 g., 16.95 mMol) is then added and the mixture is stirred for 5 more mins. $Et_3N$ (2.364 ml., 16.95 ml) is added to the mixture and stirring is continued for 30 more mins. at room temperature. Anhydrous, powdered $K_2CO_3$ (4.70 g., 34 mMol) is added and stirring is continued for a further 65 mins. The mixture is filtered and the filtrate is concentrated in vacuo. The residue is taken up in $CH_2Cl_2$, washed with $H_2O$ (2x) and brine, dried with $MgSO_4$, filtered, and evaporated in vacuo to provide crude p-nitrobenzyl 2-methylthio-5-hydroxy-5-acetoxymethyl-5,6-dihydro-4H-1,3-thiazine-4-carboxylate (6.31 g.) as a dark oil: ir(neat) 2.96, 5.72, 5.77, 6.22, 6.30, 6.56, 7.40, 8.10, 10.91, and 13.6μ; nmr $(CDCl_3)\delta$ 2.12 (s, 3, CO$CH_3$), 2.42 (s, 3, S$CH_3$), 3.03, 3.28 (ABq, 2, J=12Hz, S$CH_2$), 4.25 (s, 2, $CH_2$OAc), 4.75 (splintered s, 1, H4, small coupling with upfield S$CH_2$ proton), 5.37 (s, 2, $CH_2$Ar), and 7.57, 8.25 (ABq, 4, J=9, Ar$H$).

Step C: p-Nitrobenzyl 7-azido-6-methylthio-3-hydroxy-3-acetoxymethyl-cepham-4-carboxylate A solution of crude p-nitrobenzyl 2-methylthio-5-hydroxy-5-acetoxymethyl-5,6-dihydro-4H-1,3-thiazine-4-carboxylate (6.31 g., 15.23 mMol) in anydyrous $CH_2Cl_2$ (75 ml.) is cooled to $-78°$ C. under a $N_2$ atmosphere. $Et_3N$ (2.97 ml., 21.3 mMol) is added to the stirring solution followed by dropwise addition of a solution of azidoacetyl chloride (1.85 ml., 21.2 mMol) in $CH_2Cl_2$ (20 ml.). The resulting solution is allowed to warm slowly to room temperature. The solution is washed with $H_2O$ (3x) and brine, dried with $MgSO_4$, filtered, and concentrated in vacuo to a dark, reddish-brown, viscous oil (7.3 g.). This material is purified by chromatography on silica gel (140 g.). Elution of the column with 10% EtOAc/Oh provides p-nitrobenzyl 7-azido-6-methylthio-3-hydroxy-3-acetoxymethyl-cepham-4-carboxylate (4.10 g.) as a dark oil: ir ($CHCl_3$) 2.91, 4.72, 5.58, 5.73, 6.20, 6.55, and 7.39$\mu$; nmr ($CDCl_3$)$\delta$ 2.13 (s, 3, $COCH_3$), 2.23 (s, 3, $SCH_3$), 2.83, 3.63 (ABq, 2, J=14Hz, $SCH_2$), 4.17 (s, 1, OH), 4.30, 4.57 (ABq, 2, J=12Hz, $CH_2OAc$), 4.87 (s, 2, H4 and H7), 5.37 (s, 2, $CH_2Ar$), and 7.60, 8.25 (ABq, 4, J=9Hz, ArH); mass spectrum m/e 497 (M+), 469, 454, 422, 414, 368, 354, 341, 311, 299, 278, 261, and 136.

Step D: p-Nitrobenzyl 7-azido-6-methylthio-3-acetoxymethyl-3-methylsulfonyloxy-cepham 4-carboxylate To an ice-cold, stirring solution of p-nitrobenzyl 7-azido-6-methylthio-3-acetoxymethyl-3-hydroxy-cepham-4-carboxylate (2.72 g., 5.47 mMol) and $Et_3N$ (1.15 ml., 8.25 mMol) in anhydrous $CH_2Cl_2$ (20 ml.) is added dropwise a solution of methanesulfonyl chloride (0.51 ml., 6.56 mMol) in anhydrous $CH_2Cl_2$ (15 ml.). After stirring 15 more mins. in the cold, the solution is washed with $H_2O$, 5% HCl, 5% $NaHCO_3$, and brine, dried with $MgSO_4$, filtered, and evaporated in vacuo. The residual oil is crystallized from $CH_2Cl_2$—MeOh to afford p-nitrobenzyl 7-azido-6-methylthio-3-acetoxymethyl-3-methylsulfonyloxycepham-4-carboxylate (2.15 g.) as yellow crystals: mp 147° C.; ir ($CHCl_3$) 4.72, 5.59, 5.71, 6.58 and 7.42$\mu$; nmr ($CDCl_3$)$\delta$ 2.17 (s, 3, $COCH_3$), 2.20 (s, 3, $SCH_3$), 3.00 (s, 3, $SO_2CH_3$), 3.22, 4.28 (ABq, 2, J=14Hz, $SCH_2$, 4.67, 4.95 (ABq, 2, J=13Hz, $CH_2OAc$), 4.88 (s, 1, H7), 5.20 (s, 1, H4), 5.35 (s, 2, $CH_2Ar$), and 7.63, 8.25 (ABq, 4, J=9, ArH).

Anal. calculated for $C_{19}H_{21}O_{10}N_5S_3$: C, 39.65; H, 3.68; N, 12.17; S, 16.17. Found: C, 39.62; H, 3.59; N, 12.17; S, 16.76.

Step E: p-Nitrobenzyl 7-azido-6-methylthio-3-acetoxymethyl-ceph-3-em-4-carboxylate A solution of p-nitrobenzyl 7-azido-6-methylthio-3-acetoxymethyl-3-methylsulfonyloxy-cepham-4-carboxylate (211 mg., 0.366 mMol) and $Et_3N$ (102 $\mu$l., 0.732 mMol) in anhydrous $CH_2Cl_2$ (2 ml.) is stirred at room temperature for 35 mins. The solution is washed with $H_2O$ (2x), 10% HCl, $H_2O$, and brine, dried with $MgSO_4$, filtered, and evaporated in vacuo to yield p-nitrobenzyl 7-azido-6-methylthio-3-acetoxymethyl-ceph-3-em-4-carboxylate (169 mg.) as an oil: ir (neat) 4.72, 5.59, 5.75, 6.55, and 7.40$\mu$; nmr ($CDCl_3$) 2.08 (s, 3, $COCH_3$, 2.18 (s, 3, $SCH_3$), 3.43, 3.95 (ABq, 2, J=19Hz, $SCH_2$), 4.77 (s, 1, H7) 4.83, 5.17 (ABq, 2, J=14Hz, $CH_2OAc$), 5.38 (s, 2, $CH_2Ar$), and 7.57, 8.23 (ABq, 4, J=8.5Hz, ArH); mass spectrum m/e 479 (M+), 451, 436, 404, 392, 271, 260, 216, 200, and 136.

Step E: p-nitrobenzyl 7-azido-6-methylthio-3-acetoxymethyl-ceph-3-em-4-carboxylate A mixture of p-nitrobenzyl 7-azido-6-methylthio-3-acetoxymethyl-3-methylsulfonyloxy-cepham-4-carboxylate (20 mg.) and EM silica gel 60 (500 mg.) in 3:1 $\phi$H-EtOAc (1 ml.) is stirred at room temperature for 4 hours. The mixture is diluted with EtOAc (3 ml.) and filtered through a small sintered glass funnel containing a pad of $MgSO_4$. The silica gel is washed with more EtOAc (2 × 2 ml.). Evaporation of the filtrate in vacuo provides a 3:7 mixture (19 mg.) of starting material and p-nitrobenzyl 7-azido-6-methylthio-3-acetoxymethyl-ceph-3-em-4-carboxylate.

Step F: 7-amino-6-methylthio-3-acetoxymethyl-ceph-3-em-4-carboxylic acid

A suspension of 5% palladium on powdered charcoal (360 mg.) in EtOH (6 ml.) is hydrogenated at 40 psi for 30 mins. The catalyst is collected by centrifugation, washed twice with MeOH, and suspended in MeOH (2 ml.). A solution of p-nitrobenzyl 7-azido-6-methylthio-3-acetoxymethyl-ceph-3-em-4-carboxylate (180 mg.) in THF (2 ml.) is added to the catalyst suspension and the mixture is hydrogenated at 40 psi for 1.5 hrs. The mixture is filtered and the catalyst is washed with several portions of MeOH. The combined filtrate and washings is evaporated in vacuo to provide crude product (97 mg.) Trituration of this material with $Et_2O$ affords 7-amino-6-methylthio-3-acetoxymethyl-ceph-3-em-4-carboxylic acid (87 mg.) as pale yellow crystals: ir (Nujol) 5.53, 5.60, 5.76, and 6.20$\mu$; nmr ($D_2O$ + $NaHCO_3$) $\delta$ 2.20 (s, 3, $COCH_3$), 2.22 (s, 3, $SCH_3$), 3.42, 3.90 (ABq, 2, J=18Hz, $SCH_2$), 4.53 (s, 1, H7), 4.67, 5.05 (ABq, 2, J=19Hz, $CH_2OAc$), and 4.77 (s, $HOD$).

Step G: Sodium 7-(2-thienylacetamido)-6-methylthio-3-acetoxymethyl-ceph-3-em-4-carboxylate 2-Thienylacetyl chloride (28 $\mu$l, 0.209 mMol) is added to an ice-cold, stirring mixture of 7-amino-6-methylthio-3-acetoxymethyl-ceph-3-em-4-carboxylic acid (66.4 mg., 0.209 mMol) and $NaHCO_3$ (35 mg., 0.418 mMol) in $H_2O$ (1.5 ml.) and acetone (3.0 ml.). After stirring for 30 mins. in the cold, the mixture is evaporated under reduced pressure to remove acetone. The aqueous residue is diluted with more $H_2O$ (4.5 ml). and extracted with three portions of $Et_2O$. The aqueous phase is acidified to pH 2.5 with 10% HCl and extracted with three portions of EtOAc. The EtOAc solution is dried over $MgSO_4$, filtered, and evaporated in vacuo to a solid (72 mg.). This material is extracted with $\phi$H to remove 2-thienylacetic acid and the residue recrystallized from $CH_3CN$-$Et_2O$ to provide 7-(2-thienylacetamido)-6-methylthio-3-acetoxymethyl-ceph-3-em-4-carboxylic acid (31 mg.) as an off-white solid.

The above free acid (31 mg., 0.07 mMol) is dissolved in $H_2O$ (1 ml.) containing $NaHCO_3$ (5.9 mg., 0.07 mMol) and the solution is lyophilized to yield sodium 7-(2-thienylacetamido)-6-methylthio-3-acetoxymethyl-ceph-3-em-4-carboxylate (34 mg.) as a white, amorphous powder: uv max ($H_2O$) 235 ($\epsilon$13,000) and 264 ($\epsilon$7,400) m$\mu$; nmr ($D_2O$)$\delta$ 1.90 (s, 3, $COCH_3$), 2.10 (s, 3, $SCH_3$), 3.37, 3.76 (ABq, 2, J=18Hz, $SCH_2$), 3.95 (s, 2, $CH_2$-thienyl), 4.68, 4.87 (ABq, 2, J=13Hz, $CH_2OAc$), 5.24 (s, 1, H7), 7.04 (m, 2, thienyl-H), 7.36 (m, 1, thienyl-H) and 4.64 (s, $HOD$).

In addition to the sodium salt of the 7-(2-thienylacetamido) derivative prepared in Example 1, other 7-acylamino derivatives can be easily prepared by reacting the following acylating agents with the 7-amino-6-methylthio-3-acetoxymethyl-3-cephem-4-carboxylic acid described in Step G above:
  3-thienylacetyl chloride;
  3-furylacetyl chloride;
  2-furylacetyl chloride;
  phenylacetyl chloride;
  phenyl-α-carboxylacetyl chloride;
  α-amino-phenylacetyl chloride;
  thienyl-α-carboxylacetyl chloride;
  furyl-α-carboxylacetyl chloride;
thereby yielding the analogous end products:
  7-(3-thienylacetamido)-6-methylthio-3-acetoxymethyl-3-cephem-4-carboxylic acid;
  7-(3-furylacetamido)-6-methylthio-3-acetoxymethyl-3-cephem-4-carboxylic acid;
  7-(2-furylacetamido)-6-methylthio-3-acetoxymethyl-3-cephem-4-carboxylic acid;
  7-(phenylacetamido)-6-methylthio-3-acetoxymethyl-3-cephem-4-carboxylic acid;
  7-(phenyl-α-carboxyl-acetamido)-6-methylthio-3-acetoxymethyl-3-cephem-4-carboxylic acid;
  7-(α-amino-phenylacetamido)-6-methylthio-3-acetoxymethyl-3-cephem-4-carboxylic acid;
  7-(thienyl-α-carboxyl-acetamido)-6-methylthio-3-acetoxymethyl-3-cephem-4-carboxylic acid;
  7-(furyl-α-carboxyl-acetamido)-6-methylthio-3-acetoxymethyl-3-cephem-4-carboxylic acid.

The sodium salts can be prepared or the potassium, using $KHCO_3$ or a similar salt in Step G above. Esters can be formed in a similar manner.

EXAMPLE 2

Sodium-7-(2-thienylacetamido)-6-methoxy-3-acetoxymethyl-3-cephem-4-carboxylate

Step A: p-nitrobenzyl 7-azido-6-methoxy-3-acetoxymethyl-ceph-3-em-4-carboxylate

To a vigorously stirring solution of p-nitrobenzyl 7-azido-6-methylthio-3-acetoxymethyl-3-methyl-sulfonyloxy-cepham-4-carboxylate (2.00 g., 3.48 mMol) (prepared as in Example 1, Step D), in anhydrous $CH_3CN$ (55 ml.) are added anhydrous $CH_3OH$ (25 ml.) and a solution of $Tl(ONO_2)_3 \cdot 3H_2O$ (2.78 g., 6.26 mMol) in anhydrous $CH_3OH$ (30 ml.). The resulting mixture stirred at room temperature for 5 mins., and then treated with solid $NaHCO_3$ (1.58 g., 18.77 mMol). After stirring 2 more mins., the mixture is filtered and the filtrate is evaporated in vacuo. The residue is taken up in $CH_2Cl_2$ and filtered. The $CH_2Cl_2$ filtrate is washed with $H_2O$ (2x) and brine, dried with $MgSO_4$, filtered, and evaporated in vacuo to afford crude p-nitrobenzyl 7-azido-6-methoxy-3-acetoxymethyl-3-methylsulfonyloxy-cepham-4-carboxylate (1.95 g.) as a yellow foam.

The above crude product (1.95 g.) in 3:1 φH-EtOAc (50 ml.) is stirred with EM silica gel 60 (20 g.) for 18 hrs. at room temperature. The mixture is filtered through a sintered glass funnel to remove the silica gel, which is eluted with several portions of EtOAc. Evaporation of the filtrate in vacuo leaves a yellow oil (1.50 g.). This material is chromatographed on silica gel (60 g.) using 10% EtOAc in φH as eluting solvent, to provide p-nitrobenzyl 7-azido-6-methoxy-3-acetoxymethyl-ceph-3-em-4-carboxylate (0.75 g.) as an oil: ir (neat) 4.73, 5.60, 5.74, 6.54, and 7.40μ; nmr ($CDCl_3$) δ 2.10 (s, 3, $COCH_3$), 3.32, 3.65 (ABq, 2, J=18Hz, $SCH_2$), 3.57 (s, 3, $OCH_3$), 4.37 (s, 1, H7), 4.87, 5.22 (ABq, 2, J=14Hz, $CH_2OAc$), 5.40 (s, 2, $CH_2Ar$), and 7.58, 8.22 (ABq, 4, J=9Hz, ArH).

Step B: p-Nitrobenzyl 7β-amino-6α-methoxy-3-acetoxymethyl-ceph-3em-4-carboxylate and p-nitrobenzyl 7α-amino-6α-methoxy-3-acetoxymethyl-ceph-3-em-4-carboxylate A solution of p-nitrobenzyl 7-azido-6-methoxy-3-acetoxymethyl-ceph-3-em-4-carboxylate (249 mg., 0.54 mMol) in $CHCl_3$ (5 ml.) is cooled in an ice-bath and treated with $Et_3N$ (150 μl, 1.08 mMol). $H_2S$ is bubbled through the cold solution for 2–3 mins., followed by $N_2$ for 10 mins. The resulting solution is diluted with cold $CH_2Cl_2$ (5 ml.), washed with cold dilute HCl to pH 6, cold $H_2O$ (3x) and brine, dried with $MgSO_4$, filtered, and evaporated in vacuo to provide a mixture (245 mg.) of p-nitrobenzyl 7β-amino-6α-methoxy-3-acetoxymethyl-ceph-3-em-4-carboxylate and the corresponding 7α-amino-derivative as a yellow foam.

In a separate experiment, the crude amine mixture (226 mg.) in EtOAc (1 ml.) is treated with a solution of p-toluenesulfonic acid monohydrate (98 mg., 0.52 mMol) in EtOAc (4 ml.). The resulting solution is stored at 0° C. for ca. 5 hrs., during which time a fine, white precipitate forms. The precipitate is collected, washed with cold EtOAc and hexane, and dried in vacuo to yield the p-toluenesulfonic acid salt of p-nitrobenzyl 7-amino-6-methoxy-3-acetoxymethyl-ceph-3-em-4-carboxylate (71 mg.): mp 170°–175° C. (dec.). The salt (71 mg., 0.12 mMol) is shaken with aqueous $K_2CO_3$ (18 mg., 0.13 mMol in 5 ml.) and EtOAc (5 ml.). The layers are separated and the aqueous portion is extracted with more EtOAc (3 × 3 ml.). The combined EtOAc solution is washed with brine, dried with $MgSO_4$, filtered and evaporated in vacuo to provide the major isomer of p-nitrobenzyl 7-amino-6-methoxy-3-acetoxymethyl-ceph-3-em-4-carboxylate (53 mg.) as a pale yellow oil: ir (neat) 3.97, 5.60, 5.74, 6.55, and 7.40μ; nmr ($CDCl_3$) δ 1.93 (s, 2, $NH_2$), 2.08 (s, 3, $COCH_3$), 3.25, 3.58 (ABq, 2, J=18Hz, $SCH_2$), 3.52 (s, 3, $OCH_3$), 4.28 (s, 1, H7), 4.80, 5.15 (ABq, 2, J=14Hz, $CH_2OAc$), 5.38 (s, 2, $CH_2Ar$), and 7.60, 8.23 (ABq, 4, J=9Hz, ArH); mass spectrum m/e 437 (M+), 380, 321, 257, 186, 169, and 136.

The minor amine isomer of p-nitrobenzyl 7-amino-6-methoxy-3-acetoxymethyl-ceph-3-em-4-carboxylate, has nmr ($CDCl_3$) δ 3.48 (s, 3, $OCH_3$) and 4.38 (s, 1, H7).

Step C: p-Nitrobenzyl 7β-(2-thienylacetamido)-6α-methoxy-3-acetoxymethyl-ceph-3-em-4-carboxylate and p-nitrobenzyl 7α-(2-thienylacetamido)-6α-methoxy-3acetoxymethyl-ceph-3-em-4-carboxylate A mixture of isomeric p-nitrobenzyl 7-amino-6-methoxy-3-acetoxymethyl-ceph-3em-4-carboxylate (245 mg., 0.54 mMol) in anhydrous $CH_2Cl_2$ (4 ml.) is cooled in an ice-bath and treated with pyridine (43 μl., 0.54 mMol) and 2-thienylacetyl chloride (72 μl, 0.54 mMol). After stirring in the cold for 30 mins., the reaction mixture is washed with $H_2O$ (3x) and brine, dried with $MgSO_4$, filtered, and concentrated in vacuo. The yellow, oily residue (314 mg.) is purified by preparative layer chromatography on two 0.1 × 20 × 20 cm silica gel GF plates, using 3:1 φH-EtOAc as developing solvent. Three major uv visible bands are removed and eluted with EtOAc.

Band A ($R_f$ 0.21) provides p-nitrobenzyl 7-(2-thienylacetamido)-6-methoxy-3-acetoxymethyl-ceph-2-em-4-carboxylate (47 mg.) as a yellow oil: ir (neat) 3.04, 5.61, 5.74, 5.95, 6.59, 7.42, 8.14, 10.94, and 13.64μ; nmr (CDCl$_3$) δ 2.03 (s, 3, COC$\underline{H}_3$), 3.23 (s, 3, OC$\underline{H}_3$), 3.83 (s, 2, thienyl-C$\underline{H}_2$), 4.70 (m, 2, C$\underline{H}_2$OAc), 5.20 m, 1, H4), 5.28 (s, 2, C$\underline{H}_2$Ar), 5.50 (d, 1, J=9Hz, H7), 6.48 (m, 1, H2), 6.53 (d,1 J=9Hz, N$\underline{H}$), 6.98 (m, 2, thienyl-$\underline{H}$), 7.27 (m, 1, thienyl-$\underline{H}$), and 7.50, 8.20 (ABq, 4, J=9Hz, Ar$\underline{H}$).

Band B (R$_f$ 0.30) provides the major isomer of p-nitrobenzyl 7-(2-thienylacetamido)-6-methoxy-3-acetoxymethylceph-3-em-4-carboxylate (77 mg.) as a pale yellow oil.

Band C (R$_f$ 0.42) provides the minor isomer of p-nitrobenzyl 7-(2-thienylacetamido)-6-methoxy-3-acetoxymethylceph-3-em-4-carboxylate (39 mg.) as a pale yellow oil: ir (neat) 3.09, 5.60, 5.75, 5.94, 6.57, 7.40, 8.06, 10.88, 11.67, and 13.55μ; nmr (CDCl$_3$ δ 2.07 (s, 3, COC$\underline{H}_3$), 3.38 (m, 2, SC$\underline{H}_2$), 3.52 (s, 3, OC$\underline{H}_3$), 3.83 (s, 2, thienyl-C$\underline{H}_2$), 4.85, 5.18 (ABq, 2, J=13Hz, C$\underline{H}_2$OAc), 5.53 (s, 2, C$\underline{H}_2$Ar), 5.50 (d, 1, J=9Hz, H7), 6.43 (d, 1, J=9Hz, N$\underline{H}$), 6.97 (m, 2, thienyl-$\underline{H}$), 7.27 (m, 1, thienyl-$\underline{H}$), and 7.53, 8.20 (ABq, 4, J=9Hz, Ar$\underline{H}$).

Step C: p-Nitrobenzyl 7-(2-thienylacetamido)-6-methoxy-3-acetoxymethyl-ceph-3-em-4-carboxylate A solution of the major isomer of p-nitrobenzyl 7-amino-6-methoxy-3-acetoxymethyl-ceph-3-em-4-carboxylate (53 mg., 0.12 mMol) in anhydrous CH$_2$Cl$_2$ (1 ml.) is cooled in an ice-bath and treated with pyridine (10.7 μl, 0.13 mMol) and 2-thienylacetyl chloride (17.8 μl., 0.13 mMol). The resulting solution is stirred in the cold for 30 mins., and then diluted with CH$_2$Cl$_2$, washed with H$_2$O (3x) and brine, dried with MgSO$_4$, filtered, and evaporated in vacuo. Crystallization of the residual yellow oil (66 mg.) from CH$_2$Cl$_2$ - hexane affords p-nitrobenzyl 7-(2-thienylacetamido)-6-methoxy-3-acetoxymethyl-ceph-3-em-4-carboxylate as off-white crystals: mp 148°–151° C.; ir (neat) 3.04, 5.57, 5.74, 5.91, 6.54, 7.40, 8.1, 11.67, and 13.5μ; nmr (CDCl$_3$) δ 2.05 (s, 3, COC$\underline{H}_3$), 3.23 (s, 3, OC$\underline{H}_3$), 3.38 (s, 2, SC$\underline{H}_2$), 3.82 (s, 2, thienyl-C$\underline{H}_2$), 4.75, 5.10 (ABq, 2, J=13Hz, C$\underline{H}_2$OAc), 5.32 (d, 1, J=9Hz, H7), 5.35 (s, 2, C$\underline{H}_2$Ar), 6.82 (d, 1, J=9Hz, N$\underline{H}$), 6.95 (m, 2, thienyl-$\underline{H}$), 7.23 (m, 1, thienyl-$\underline{H}$), and 7.53, 8.17 (ABq, 4, J=9Hz, Ar$\underline{H}$); mass spectrum m/e 561 (M+), 381, 365, 321, and 200.

Anal. Calculated for C$_{24}$H$_{23}$N$_3$O$_9$S$_2$: C, 51.33; H, 4.13; N, 7.48. Found: C, 50.96; H, 4.14; N, 7.27.

Step D: Sodium 7-(2-thienylacetamido)-6-methoxy-3-acetoxymethyl-ceph-3-em-4-carboxylate A mixture of 5% Pd on charcoal (120 mg., prereduced in 1:1 THF-MeOH), the major isomer of p-nitrobenzyl 7-(2-thienylacetamido)-6-methoxy-3-acetoxymethyl-ceph-3-em-4-carboxylate (60 mg.), and 1:1 THF-MeOH (3 ml.) is hydrogenated at atmospheric pressure and room temperature for 3 hrs. The mixture is filtered and the filtrate is evaporated in vacuo. Trituration of the residue with Et$_2$O provides a white solid (50 mg.). The solid is taken up in EtOAc (5 ml.) and filtered. The EtOAc filtrate is extracted with saturated aqueous NaHCO$_3$ (3 × 2 ml.). The combined extracts are acidified to pH 2 with 10% HCl and extracted with EtOAc (4 × 3 ml.). The EtOAc extracts are washed with brine, dried over MgSO$_4$, filtered, and evaporated in vacuo to yield 7-(2-thienylacetamido)-6-methoxy-3-acetoxymethyl-ceph-3-em-4-carboxylic acid (34 mg.) as a white solid.

The free acid (34 mg., 0.080 mMol) is dissolved in H$_2$O (5 ml.) containing NaHCO$_3$ (7 mg., 0.083 mMol) and the solution is lyophilized to afford sodium 7-(2-thienylacetamido)-6-methoxy-3-acetoxymethyl-ceph-3-em-4-carboxylate (40 mg.) as an amorphous, white powder: ir (Nujol) 5.66, 5.78, 5.96, and 6.21μ; uv max (H$_2$O) 232 (ε12,700) and 265 (ε7,200) mμ; nmr (D$_2$O) δ 2.08 (s, 3, COC$\underline{H}_3$), 3.22 (s, 3, OC$\underline{H}_3$), 3.29, 3.52 (ABq, 2, J=17Hz, SC$\underline{H}_2$), 3.92 (s, 2, thienyl-C$\underline{H}_2$), 4.66, 4.85 (ABq, 2, J=12Hz, C$\underline{H}_2$OAc), 5.17 (s, 1, H7). 7.00 (m, 2, thienyl-$\underline{H}$), 7.31 (m, 1, thienyl-$\underline{H}$), and 4.66 (s, $\underline{H}$OD).

Step E: Sodium 7-(2-thienylacetamido)-6-methoxy-3-acetoxymethyl-ceph-3-em-4-carboxylate A mixture of the minor isomer of p-nitrobenzyl 7-(2-thienylacetamido)-6-methoxy-3-acetoxymethyl-ceph-3-em-4-carboxylate (50 mg.), 5% pd on charcoal (100 mg., prereduced in 1:1 THF-MeOH), and 1:1 MeOH-THF (3 ml.) is hydrogenated at atmospheric pressure and room temperature for 3 hrs. Work-up as described in Step D above provides sodium 7-(2-thienylacetamido)-6-methoxy-3-acetoxymethyl-ceph-3-em-4-carboxylate (15 mg.) as an amorphous powder.

EXAMPLE 3

In order to prepare other 3-substituted compounds, the following procedure can be used:

The final products of either of Examples 1 or 2, e.g., that described in Example 1 G, sodium 7-(2-thienylacetamido)-6-methylthio-3-acetoxymethyl-3-cephem-4-carboxylate (0.31 g.) can be treated by dissolving in citrus acetyl esterase (8.5 ml.). The solution is stirred in a water bath maintained at 30° C., and the pH is kept at 6.6 by addition of 1 N sodium hydroxide. After 1 hour, additional enzyme solution (1.5 ml.) is added. The pH is maintained at 6.6 until it remains constant for ca. 0.5 hour. After cooling to room temperature, the solution is treated with sodium chloride (3.0 g.), layered with ethyl acetate (10 ml.), and acidified to pH 2.1 with 6 N hydrochloric acid. The ethyl acetate portion is separated and washed with water. The organic phase is then layered with water (25 ml.) and the pH is adjusted to 5.6 with 6 N potassium hydroxide. The aqueous phase is separated and lyophilized. Recrystallization of the residue from methanol-isopropanol affords potassium 6-methylthio-7-(2-thienylacetamido)-3-hydroxymethyl-3-cephem-4-carboxylate. The analogous potassium 6α-methoxy-7-(α or β)-(2-thienylacetamido)-3-hydroxymethyl-3-cephem-4-carboxylate is prepared in a similar fashion using either the products described in Example 2D or 2E.

These 3-hydroxymethyl intermediates (0.20 g.) can then be reacted with chlorosulfonyl isocyanate, 0.15 ml., in 5 ml. acetonitrile. The resulting mixture is stirred in the cold for 90 minutes. Evaporation of the solvent leaves a residue which is taken up in ethyl acetate (10 ml.) and water (10 ml.). The pH of the aqueous layer is adjusted to 1.6 with 2.5 N hydrochloric acid and the mixture is stirred for 2.5 hours at room temperature. The pH is then adjusted to 8 with aqueous tripotassium phosphate. The aqueous phase is separated, acidified to pH 2.5 with hydrochloric acid, and extracted with ethyl acetate. The ethyl acetate solution, after drying over sodium sulfate, is evaporated in vacuo to give 6-methoxy or (6-methylthio)-7-(2-thienylacetamido)-3-carbamoyloxymethyl-3-cephem-4-carboxylic acid.

The acetyl esterase and acetoxy esterase cleavages can also be done on the 7-amino-6-methoxy or methylthio intermediates of Examples 1 and 2, thereby producing the desired 3-CH$_2$A compounds which can be acylated as desired.

The heteroarylthio derivatives can be made by displacing the 3-acetoxymethyl group with either of N-methyltriazinyl mercaptan, N-methyl-1,2,3,4-tetrazoyl mercaptan, or 5-methyl-1,3,4-thiadiazoyl mercaptan, using approximately equimolar amounts, in the presence of a base, such as sodium bicarbonate.

What is claimed is:

1. The compound having the following formula:

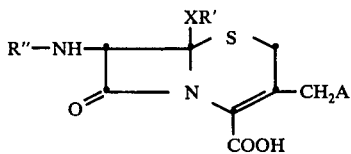

wherein X is oxygen or sulfur, R' is lower alkyl of 1-5 carbon atoms, R" is hydrogen, or

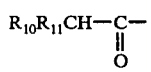

wherein $R_{10}$ is hydrogen, carboxyl, amino or hydroxy, and $R_{11}$ is phenyl, thienyl, or furyl, and A is loweralkanoyloxy of 1-5 carbon atoms or hydrogen, and the alkali metal salts, or benzyl or p-nitrobenzyl esters thereof.

2. The compound of claim 1 which is sodium 7-(2-thienylacetamido)-6-methylthio-3-acetoxymethyl-3-cephem-4-carboxylate.

3. The compound of claim 1 which is sodium 7-(2-thienylacetamido)-6-methoxy-3-acetoxymethyl-3-cephem-4-carboxylate.

4. The compound of claim 1 which is sodium 7-(phenylacetamido)-6-methoxy-3-acetoxymethyl-3-cephem-4-carboxylate.

5. The compound of claim 1 which is p-nitrobenzyl 7-amino-6-methoxy-3-acetoxymethyl-3-cephem-4-carboxylate.

6. The compound of claim 1 which is benzyl 7-amino-6-methoxy-3-acetoxymethyl-3-cephem-4-carboxylate.

7. The compound of claim 1 which is 7-amino-6-methylthio-3-acetoxymethyl-3-cephem-4-carboxylic acid.

8. The process which comprises reacting a compound of the formula:

$$H_2N-CH_2-COOM$$

wherein M is benzyl, or p-nitrobenzyl; with carbon disulfide, then loweralkyl iodide; then treating the resulting reaction product with a substituted acetone of the formula

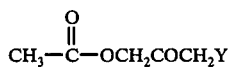

wherein Y is chloro or iodo; in the presence of 1-5 equivalents of base, and reacting the resulting product with an azido acetyl reagent of the formula

wherein Z is halogen, $OSO_2CF_3$ or $OSO_2CH_3$, in the presence of a base to produce a dl-7-azido-6-cephalosporin compound of the formula:

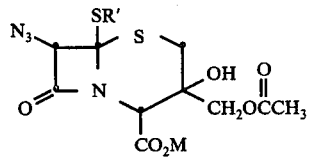

wherein R' is loweralkyl of 1-5 carbon atoms and M is as defined above;

reacting this product with methylsulfonyl chloride to prepare the analogous 3-methylsulfonyloxy derivative

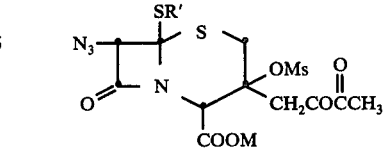

wherein R' and M are as defined and Ms is methylsulfonyl; followed by dehydration using either triethylamine in methylene chloride or silica gel to yield the desired product

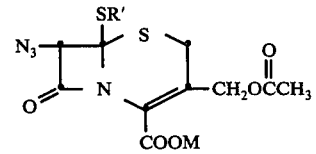

wherein R' is loweralkyl of 1-5 carbon atoms and M is benzyl, or p-nitrobenzyl.

9. The process of claim 8 in which the 3 methylsulfonyloxy derivative is reacted with thallium nitrate in the presence of methanol to yield the compound

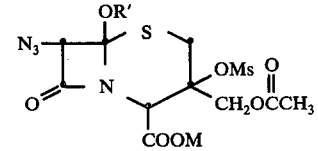

10. The process of preparing the compound of the formula

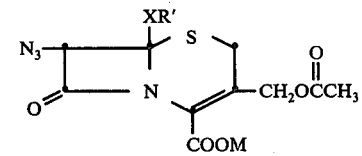

in which R' is loweralkyl of 1-5 carbon atoms, M is benzyl or p-nitrobenzyl, and X is oxygen or sulfur, which comprises treating the compound of the formula

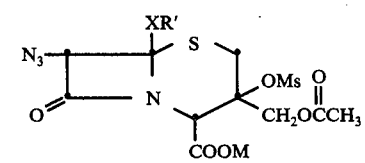

with either triethylamine in the methylene chloride or silica gel to produce the desired product.

* * * * *